(12) United States Patent
Lavoritano et al.

(10) Patent No.: US 11,684,390 B2
(45) Date of Patent: Jun. 27, 2023

(54) FEMALE POLYAXIAL JOINT AND METHOD OF USING SAME

(71) Applicant: DePuy Synthes Products, Inc., Raynham, MA (US)

(72) Inventors: Scott Lavoritano, West Chester, PA (US); Albert Montello, West Chester, PA (US); James Hearn, West Chester, PA (US); Christoph Notzli, Davos Platz (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/143,480

(22) Filed: Jan. 7, 2021

(65) Prior Publication Data

US 2022/0211414 A1 Jul. 7, 2022

(51) Int. Cl.
*A61B 17/64* (2006.01)
*A61B 17/62* (2006.01)
*A61B 17/56* (2006.01)

(52) U.S. Cl.
CPC .......... *A61B 17/6425* (2013.01); *A61B 17/62* (2013.01); *A61B 2017/564* (2013.01)

(58) Field of Classification Search
CPC ... A61B 17/6425; A61B 17/62; A61B 17/564; A61B 2017/564
USPC .............................................. 606/54, 55, 56
See application file for complete search history.

(56) References Cited

U.S. PATENT DOCUMENTS

| | | | |
|---|---|---|---|
| 4,920,959 A | 5/1990 | Witzel et al. | |
| 8,062,293 B2 | 11/2011 | Steiner et al. | |
| 9,078,700 B2 | 7/2015 | Ross et al. | |
| 9,936,975 B2* | 4/2018 | Siemer | A61B 17/6416 |
| 2010/0331840 A1* | 12/2010 | Ross | A61B 17/62 606/54 |
| 2013/0018374 A1* | 1/2013 | Edelhauser | A61B 17/62 606/56 |
| 2018/0303635 A1* | 10/2018 | Haun | A61F 2/76 |
| 2020/0000492 A1* | 1/2020 | Samchukov | A61B 17/66 |
| 2020/0360057 A1 | 11/2020 | Samchukov et al. | |

FOREIGN PATENT DOCUMENTS

WO 2017150782 A1 9/2017

OTHER PUBLICATIONS

International Search Report, dated Feb. 10, 2022, in PCT/IB2021/061514, filed Dec. 9, 2021.
Written Opinion of the International Searching Authority, dated Feb. 10, 2022, in PCT/IB2021/061514, filed Dec. 9, 2021.

* cited by examiner

*Primary Examiner* — Eduardo C Robert
*Assistant Examiner* — David C Comstock
(74) *Attorney, Agent, or Firm* — Dunlap Codding, P.C.

(57) ABSTRACT

Female polyaxial joints for connecting a strut to a support frame of an external fixation device are described having a ball socket and a ball member. The ball member includes a spherical portion and a ball member shaft extending from the spherical portion. At least one aperture is positioned on the ball member and traverses through at least a portion of the ball member shaft. An internal surface of the ball member shaft may be threaded and configured to receive a threaded connector.

20 Claims, 8 Drawing Sheets

FEMALE POLYAXIAL JOINT AND METHOD OF USING SAME

BACKGROUND

External fixation is a surgical treatment wherein pins or wires may be percutaneously placed through a body of a patient to secure an external scaffolding device, such that at least a portion of the stabilizing structure is positioned on the outside of the body of the patient. The external fixator may be used to stabilize fractured limbs, for example, in proper position. External fixator treatments may cause less disruption of soft tissue as compared to use of internal plates and intramedullary nails used in internal fixation treatments as the components used to provide stability are positioned entirely within a patient's body. Additionally, external fixation treatments may be used in soft tissue management resulting from acute or chronic trauma wherein skin quality may be compromised. Further, the temporary nature of pins and wires used in external fixation treatments may provide bone stability in cases of bone infection wherein the presence of entirely internal implants may make treatment of the infection challenging.

One type of external fixation treatment includes a circular frame fixator. Generally, the basic components of the circular frame fixator include rings, connecting rods, and struts. The frame encircles a limb and is attached to bone by pins inserted through the bone and limb. External rings may be linked to each other by the rods and struts allowing for movement of bone fragments without opening of a fracture site. The bone fragments can then be fixed in a rigid position for healing. Within the industry, the classic circular frame fixator is the Ilizarov external fixator.

The Ilizarov external fixator may be integrated with other circular frames, such as the Taylor Spatial Frame (TSF), for example. The TSF is a hexapod device that includes two or more aluminum or carbon fiber rings connected by struts. Each strut may be independently lengthened or shortened to achieve the desired results (e.g., compression at the fracture site, lengthening of bone segments). The TSF may be connected to the bone by wire or half pins. The attached bone segments may be manipulated in different axes and degrees of freedom such that angular, translational, rotational and length deformities may be corrected.

Polyaxial struts may be used within a circular frame to accommodate non-orthogonal orientations. To ease the process of building such frames, the struts may be constructed using the polyaxial joints to swivel and maintain orientation set by the surgeon rather than gravity. During building of the frame, strut angulation and positioning may be manipulated prior to fixing the strut to the frame.

Currently, two different types of struts exist in the marketplace for strut ring fixator frames: linear struts and polyaxial struts. This creates an added cost for manufacturers and flexibility of surgeons. Accordingly, a strut configured to behave as a linear and a polyaxial strut may be desirable using polyaxial joints. Further, having a polyaxial joint allowing for ease in removal of the polyaxial strut may be beneficial during treatment.

DETAILED DESCRIPTION

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions, assemblies, systems, kits, and/or methods disclosed herein can be made and executed without undue experimentation in light of the present disclosure. While the compositions, assemblies, systems, kits, and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "patient" as used herein includes human and veterinary subjects. "Mammal" for purposes of treatment refers to any animal classified as a mammal, including (but not limited to) humans, domestic and farm animals, nonhuman primates, and any other animal that has mammary tissue. In some embodiments, the term "patient" may apply to a simulation mannequin for use in teaching, for example.

The term "treatment" refers to both therapeutic treatment and prophylactic or preventative measures. Those in need of treatment include, but are not limited to, individuals already having a particular condition/disease/infection as well as individuals who are at risk of acquiring a particular condition/disease/infection (e.g., those needing prophylactic/preventative measures). The term "treating" refers to administering an agent/element/method to a patient for therapeutic and/or prophylactic/preventative purposes.

Administering a therapy in relation to external fixation treatment is intended to provide a therapeutic benefit in the treatment, prevention, and/or management of a disease, condition, and/or infection. The specific amount in relation to time or quantity that is therapeutically effective can be readily determined by the ordinary medical practitioner, and can vary depending on factors known in the art, such as (but not limited to) the type of condition/disease/infection, the patient's history and age, the stage of the condition/disease/infection, and the co-administration of other agents or treatments.

The term "effective amount" refers to an amount of a treatment protocol in relation to external fixation, sufficient to exhibit a detectable therapeutic effect commensurate with a reasonable benefit/risk ratio when used in the manner of the inventive concept(s). The therapeutic effect may include, for example but not by way of limitation, preventing, inhibiting, or reducing the occurrence of a bone fracture, for example. The effective treatment for a subject will depend upon the type of subject, the subject's size and health, the nature and severity of the condition/disease/infection to be treated, the method of administration, the duration of treatment, the nature of concurrent therapy or treatment (if any), the specific formulations employed, and the like.

As used herein, the term "concurrent therapy" is used interchangeably with the terms "combination therapy" and "adjunct therapy," and will be understood to mean that the patient in need of external fixation treatment is treated or given another treatment or drug for the condition/disease/infection in conjunction with the external fixation treatment(s) of the present disclosure. This concurrent therapy can be sequential therapy, where the patient is treated first with one treatment protocol/pharmaceutical composition and then the other treatment protocol/pharmaceutical composition, or the two treatment protocols/pharmaceutical compositions are given simultaneously.

The terms "administration" and "administering," as used herein, will be understood to include all routes of administration known in the art, including but not limited to, oral, topical, transdermal, parenteral, subcutaneous, intranasal, mucosal, intramuscular, intraperitoneal, intravitreal, and intravenous routes, and including both local and systemic applications. In addition, the compositions of the present disclosure (and/or the methods of administration of same) may be designed to provide delayed, controlled, or sustained release using formulation techniques which are well known in the art.

Figure 1:
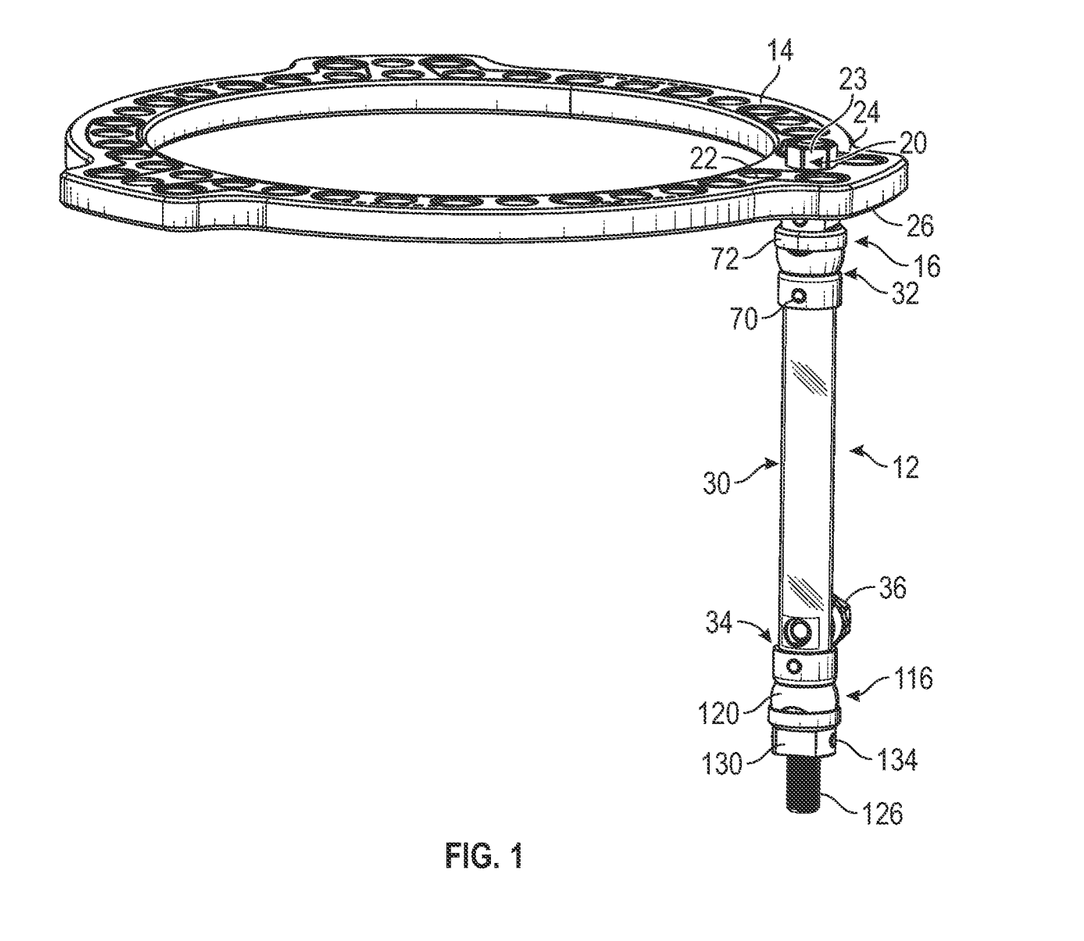
FIG. 1 is a perspective view of an exemplary external fixation device in accordance with the present disclosure.
Figure 2:
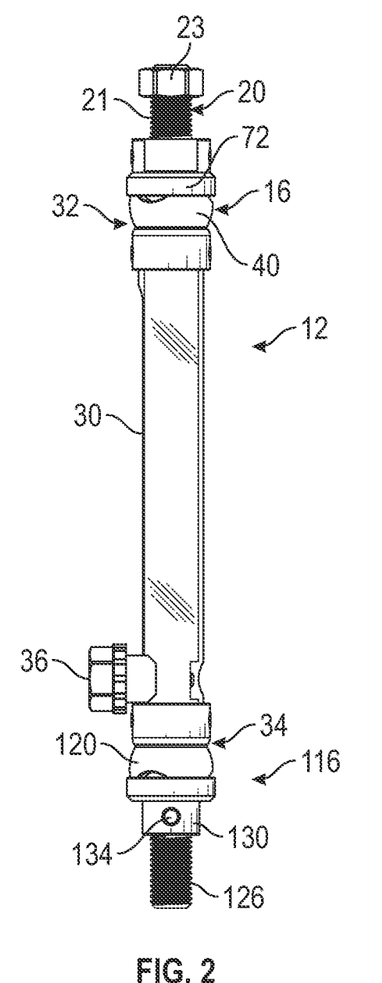
FIG. 2 is a perspective view of an exemplary strut for use in the external fixation device illustrated in FIG. 1.

Referring now to the drawings, and in particular FIGS. 1-3, shown therein is an exemplary embodiment of an external fixation device 10 in accordance with the present disclosure. The external fixation device 10 includes one or more struts 12 designed to engage with two or more support frames 14. Each strut 12 of the external fixation device 10 includes one or more female polyaxial joints 16 having an internal surface 18 configured to engage with a connector 20, such as a connector 20. When the connector 20 is a threaded connector, such as a screw or bolt, the internal surface 18 can be threaded. In this embodiment, the connector 20 being the connector 20 secures the strut 12 to the support frame 14.

As used herein, the term "support frame" 14 is used interchangeably with the term "ring" 14. The support frame 14, however, may be understood to be any shape (e.g., circular, triangular, square, fanciful, etc.) and is not limited to a circular ring shape. Further, as one skilled in the art will appreciate, the support frame 14 or ring may be a fully closed, partially open, or arch depending on treatment protocol known in the art. Diameter, thickness, and stiffness of the support frame 14 may depend on treatment protocol. Additionally, two or more support frames 14 having different diameter, thickness and/or stiffness may be used within the external fixation device 10. Distance between two or more support frames 14 may also depend on treatment protocol.

The support frame 14 includes one or more apertures 22 with each aperture 22 configured to receive a shaft 21 of the connector 20. In the example shown, the support frame 14 includes many apertures 22. For purposes of clarity, only one of the apertures 14 has been labeled in FIG. 1. The support frame 14 has a first side 24 and a second side 26. Each aperture 22 of the support frame 14 extends between the first side 24 and the second side 26. The shaft 21 of the connector 20 may be positioned in the aperture 22 and extends from the first side 24 to the second side 26 with a head fastener 23 of the connector 20 positioned on the first side 24 of the support frame 14. The shaft 21 of the connector 20 is further positioned and secured within the female polyaxial joint 16 connected at the second side 26 of the support frame 14. To that end, the connector 20 having the head fastener 23 positioned on the first side 24 of the support frame 14 and the shaft 21 of the connector 20 extending through the aperture 22 of the support frame 14 and into the female polyaxial joint 16 secures the strut 12 to the second side 26 of the support frame 14. The head fastener 23 may be provided with an external shape so as to engage with a tool (e.g., wrench or socket) for rotating the head fastener 23. For example, the external shape can be square, hexagonal, or octagonal. In other embodiments, the head fastener 23 may be provided with a slot or opening to receive the tool. The slot or opening can be of a variety of types, such as hexagonal, philips, regular, star, square or the like.

The strut 12 is an adjustable rod that may be positioned between two support frames 14. Each strut 12 may include a housing 30 extending between a first end 32 and a second end 34 of the strut 12 and is configured to be independently lengthened or shortened relative to the support frames 14 (e.g., forcing two interconnected support frames 14 towards each other, forcing two interconnected support frames 14 apart from each other). Adjustment of the strut 12 may provide for manipulation of one or more bone segments within multiple axes during treatment.

In some embodiments, the housing 30 of the strut 12 may be a telescopic housing extending from the first end 32 to the second end 34. To that end, the strut 12 may include one or more portions configured to be slidably received within one or more channels of the strut 12 allowing for adjustment of the end-to-end length of the strut 12. An adjustment mechanism 36 may be configured to allow for adjustment of end-to-end length of the strut 12 for a particular treatment protocol. The adjustment mechanism 36 may include any configuration known in the art allowing for end-to-end length adjustment of the strut 12. In some embodiments, the adjustment mechanism 36 may be a wheel configured to be gradually rotated to translate movement of a rod within the housing 30 of the strut 12 adjusting the end-to-end length of the strut 12. In some embodiments, the adjustment mechanism 36 may include a locking mechanism to prevent engagement or disengagement.

Referring to FIGS. 2 and 3, each strut 12 of the external fixation device 10 includes one or more female polyaxial joints 16 having the internal surface 18 configured to engage with the connector 20. The connector 20 secures the strut 12 to the support frame 14. In some embodiments, each strut 12 of the external fixation device 10 includes two female polyaxial joints 16 having the internal surfaces 18 configured to engage with the connectors 20 such that the first female polyaxial joint 16 is positioned at the first end 32 of the strut 12 and the second female polyaxial joint 16 is positioned at the second end 34 of the strut 12. In some embodiments, as shown in FIG. 2, the strut 12 may include the female polyaxial joint 16 having the internal surface 18 configured to engage with the connector 20 positioned at the first end 32 of the strut 12. A polyaxial stud joint 116 may be provided on the second end 34 of the strut 12. Each of the female polyaxial joint 16 and polyaxial stud joint 116 may provide for angular and rotational alignment of the strut 12 relative to the support frame 14.

Figure 3A:
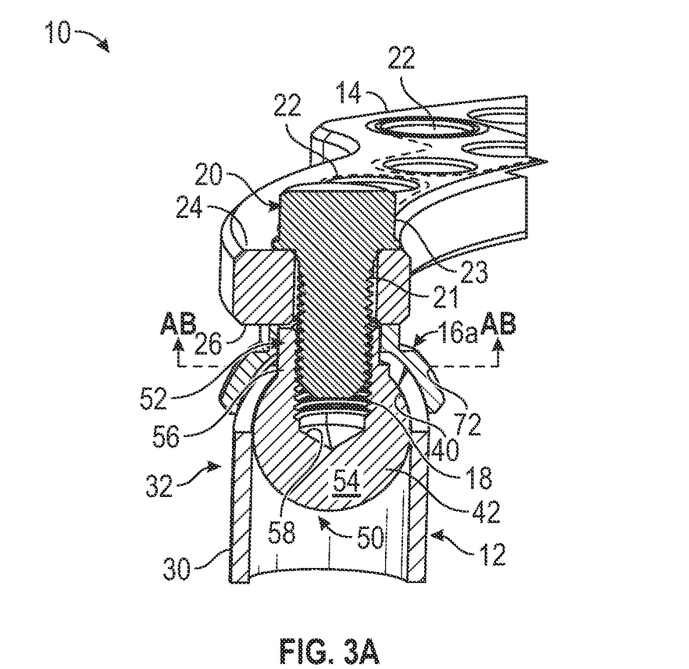
FIG. 3A is a cut-away view of an exemplary female polyaxial joint attached to a support frame in accordance with the present disclosure.
Figure 3B:
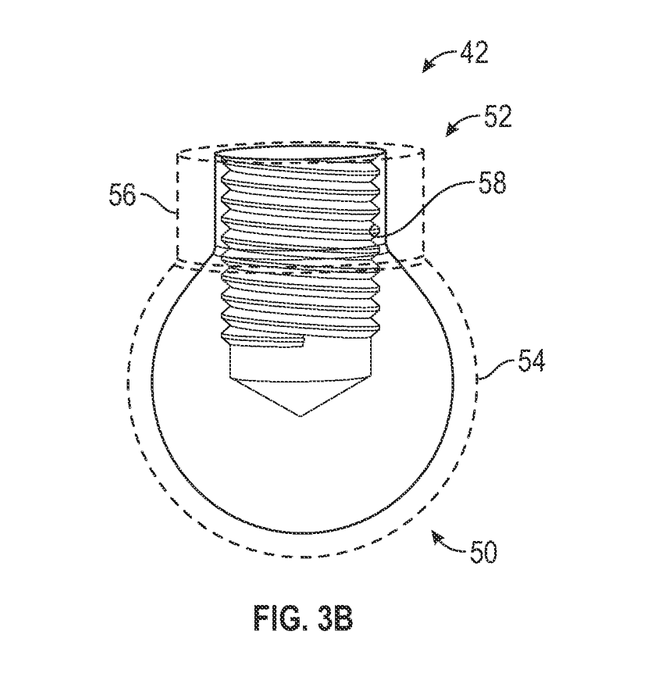
FIG. 3B is a perspective view of an exemplary ball member for use in the female polyaxial joint illustrated in FIG. 3A.
Figure 3C:
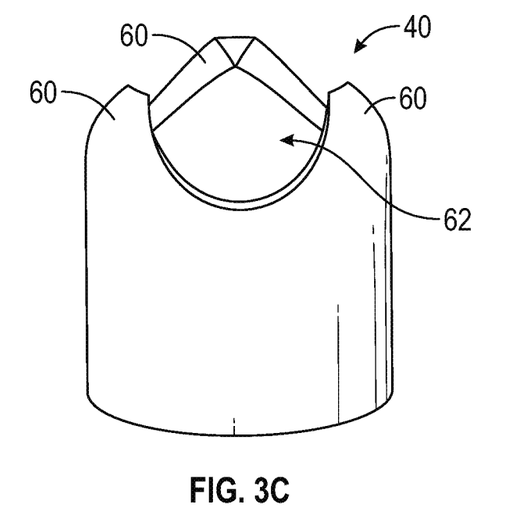
FIG. 3C is a perspective view of an exemplary ball socket for use in the female polyaxial joint illustrated in FIG. 3A.

Referring to FIGS. 3A-3C, each female polyaxial joint 16 having the internal surface 18 may include a ball socket 40 and a ball member 42. The ball member 42 may be rotatably coupled to the ball socket 40 providing pivoting movement between the strut 12 and the support frame 14.

Referring to FIG. 3B, the ball member 42 includes a first end 50 and a second end 52. A spherical portion 54 terminates at the first end 50 and extends away from the first end 50 towards the second end 52. Size and shape of the spherical portion 54 may be configured to fit within the ball socket 40 while maintaining pivoting and rotational movement of the female polyaxial joint 16, i.e., the ball socket 40 on a spherically shaped portion of the spherical portion 54. In some embodiments, a ball member shaft 56 extends from the spherical portion 54 to the second end 52 of the ball member 42. Thus, in these embodiments the spherical portion 54 terminates prior to the second end 52, and an aperture 58 is positioned at the second end 52 of the ball member 42 to provide access to the internal surface 18. The aperture 58 may extend through the ball member shaft 56 and into the spherical portion 54. In some embodiments, the aperture 58 having the internal surface 18 extends solely through the ball member shaft 56 of the ball member 42. In some embodiments, the aperture 58 having the internal surface 18 extends through the ball member shaft 56 of the ball member 42 and through at least a portion of the spherical portion 54. The aperture 58 providing access to the internal surface 18 is configured to receive the shaft 21 of the connector 20. As the shaft 21 of the connector 20 is received within the aperture 58, the ball member 42 may be drawn towards the ball socket 40 and create friction between the ball member 42 and the ball socket 40.

Referring to FIG. 3C, the ball socket 40 may partially enclose the spherical portion 54 of the ball member 42 such that the ball member 42 is operable received within the ball socket 40 while maintaining rotational movement. In some embodiments, the ball socket 40 may include one or more projections 60 configured to provide an enclosure 62 to receive the ball member 42. The one or more projections 60 may form the enclosure 62 confining the ball member 42. Each of the projections 60 may include an arcuate shape configured to matingly engage at least a portion of the spherical portion 54 of the ball member 42 The enclosure 62 may have a diameter less than the diameter of the spherical portion 54 of the ball member 42 such that the spherical portion 54 of the ball member 42 is confined within the enclosure 62 yet capable of rotation about a number of axes. The ball member shaft 56 of the ball member extends beyond the enclosure 62.

Figure 3D:
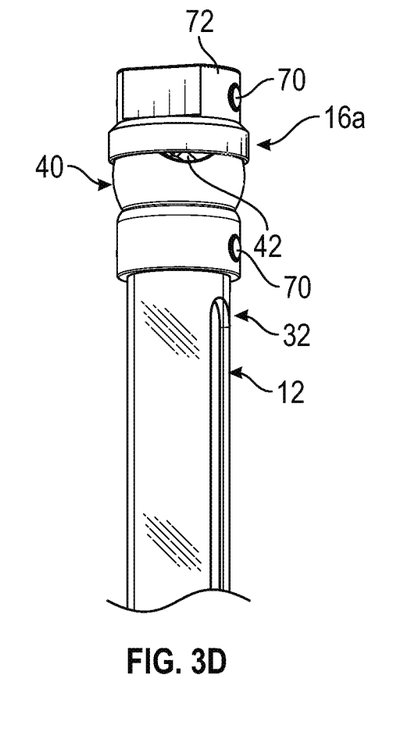
FIG. 3D is a perspective view of an exemplary polyaxial joint in accordance with the present disclosure.

Referring to FIGS. 3A and 3C, in some embodiments, the ball socket 40 may be formed in the first end 32 and/or the second end 34 of the strut 12. To that end, the ball member 42 may be rotatably coupled within the first end 32 and/or the second end 34 of the strut 12 providing pivoting movement between the housing 30 of the strut 12 and the support frame 14 (i.e., via the connector 20). For example, the first end 32 of the strut 12 may include the one or more projections 60 forming the enclosure 62 having a diameter less than a diameter of the ball member 42 such that the ball member 42 is confined within the enclosure while capable of rotation about a number of axes. In some embodiments, the ball socket 40 may be separate from the strut 12 and connected to the strut 12 via one or more securing mechanisms 70 as illustrated in FIG. 3D. The securing mechanism 70 may use any type of fastener and/or head fastener.

The female polyaxial joint 16 may also use one or more securing mechanism 70 operably connected to the strut 12 and/or one or more portions of the female polyaxial joint 16 to tighten and/or lock the female polyaxial joint 16 (e.g., ball member 42, ball socket 40). The securing mechanism(s) 70 may use any type of fastener and/or head fastener.

Figure 4A:
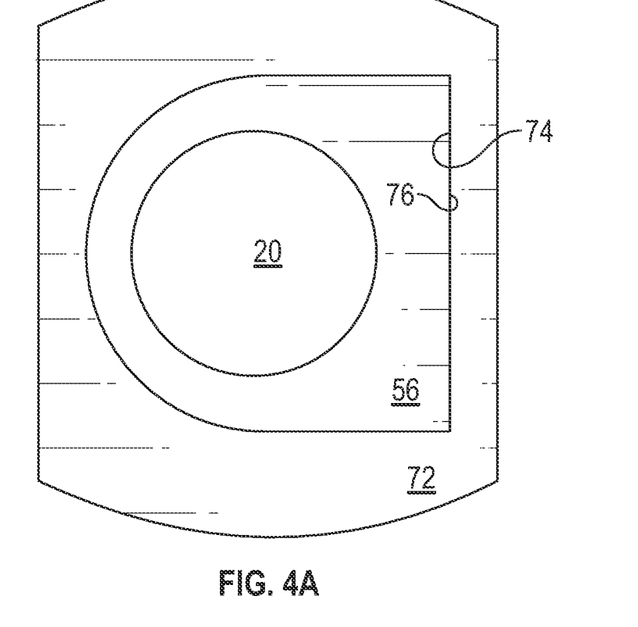
FIGS. 4A and 4B are cut-away views of the section AB illustrated in FIG. 3A.
Figure 4B:
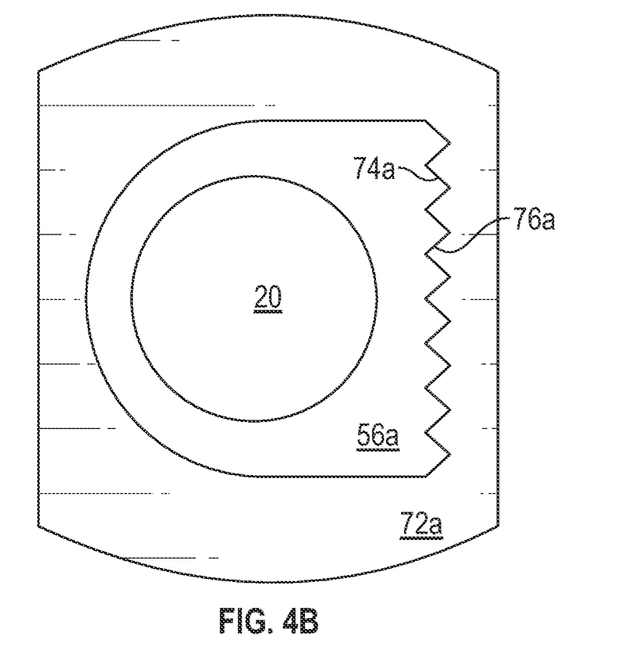

Referring to FIGS. 3D, 4A and 4B, in some embodiments, the female polyaxial joint 16 may include a collar 72. The collar 72 may be positioned between the ball socket 40 and the support frame 14. In some embodiments, the collar 72 may be positioned such that the ball member 42 of the female polyaxial joint 16 is separated from the support frame 14 (e.g., a gap exists between the ball member 42 of the female polyaxial joint 16 and the support frame 14).

In some embodiments, the collar 72 and the ball member 42 may be rotationally keyed and captivated with an interference fit (e.g., a stepped fit or captive fit). For example, in some embodiments, the collar 72 may provide a lock and key anti-rotation relationship with the ball member shaft 56 of the ball member 42 in that each of the ball member shaft 56 and collar 72 possess a specific complementary geometric shape that matingly engage, i.e., fit to the other. The collar 72 may use mechanical force via the lock and key anti-rotation relationship to secure the ball member shaft 56 of the ball member 42 in a stationary position in which the ball socket 40 can pivot and/or rotate about the spherical portion 54. As shown in FIG. 4A, the ball member shaft 56 of the ball member 42 may include at least one external side 74 configured to engage with at least one internal side 76 of the collar 72. FIG. 4B illustrates another exemplary embodiment of the ball member shaft 56a and the collar 72a wherein the at least one external side 74a includes a zig-zag pattern configured to engage with the corresponding geometric pattern on the at least one internal side 76a of the collar 72a. It should be noted that any complementary shape may be used. The complementary shape can be geometric or fanciful, for example.

As the connector 20 engages within the internal surface 18 via the aperture 58, friction is created between the spherical portion 54, the projections 60 of the ball socket 40 and the collar 72 locking and/or securing the female polyaxial joint 16 to the support frame 14. Additionally, as the connector 20 engages and tightens within the internal surface 18 via the aperture 58, friction is created between the collar 72 and the support frame 14 locking the strut 12 to the support frame 14.

Figure 5:
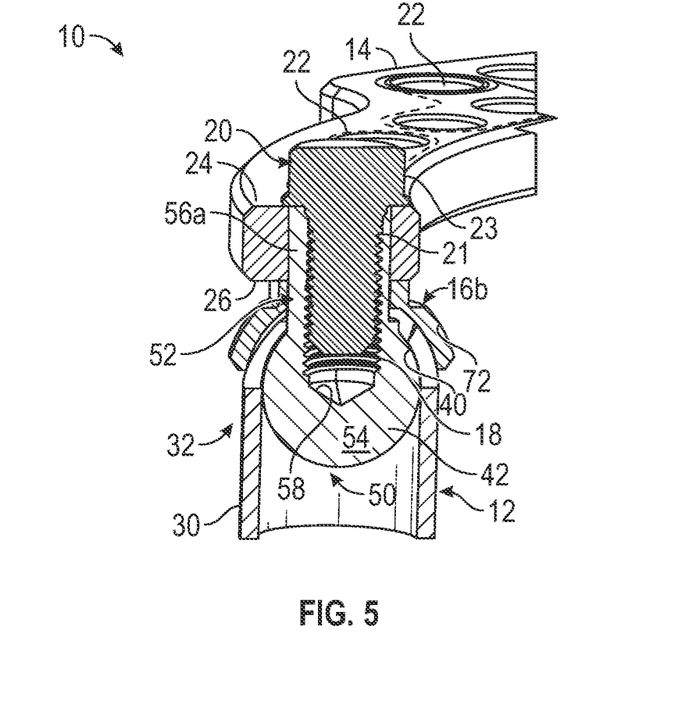
FIG. 5 is a cut-away view of another exemplary female polyaxial joint attached to a support frame in accordance with the present disclosure.

FIG. 5 illustrates another exemplary embodiment of a female polyaxial joint 16a wherein ball member shaft 56a of the ball member 42 extends through the aperture 22 of the support frame 14 from the second side 26 to the first side 24. In some embodiments, the ball member shaft 56a of the ball member 42 may extend such that the ball member shaft 56a is flush (i.e., level or even) with the first side 24 of the support frame 14. In some embodiments, the ball member shaft 56a of the ball member 42 may extend into at least a portion of the aperture 22 from the second side 26 towards the first side 24. The connector 20 may secure the female polyaxial joint 16a via engagement with the internal surface 18.

Referring to FIG. 2 and FIGS. 6A-6C, illustrated therein are exemplary embodiments of the polyaxial stud joint 116. Generally, the polyaxial stud joint 116 includes a ball joint body 120 and ball joint stud member 122 rotatably coupled to the ball joint body 120. The ball joint stud member 122 may include a ball member 124 and a shaft 126. The ball joint body 120 may include a plurality of grooves 128 configured to accommodate the shaft 126 of the ball joint stud member 122. The plurality of grooves 128 may also allow for acute angulation of the ball joint stud member 122 within the ball joint body 120 at specific angular positions as set by the surgeon. The polyaxial stud joint 116 may also include a ring contact portion 130. The ring contact portion 130 may be attached to the ball joint stud member 122 using a pin 132, for example, to inhibit rotation of the ball joint stud member 122 within the ring contact portion 130. The shaft 126 may include a threaded surface to secure the strut 12 to the support frame 14.

Figure 6A:
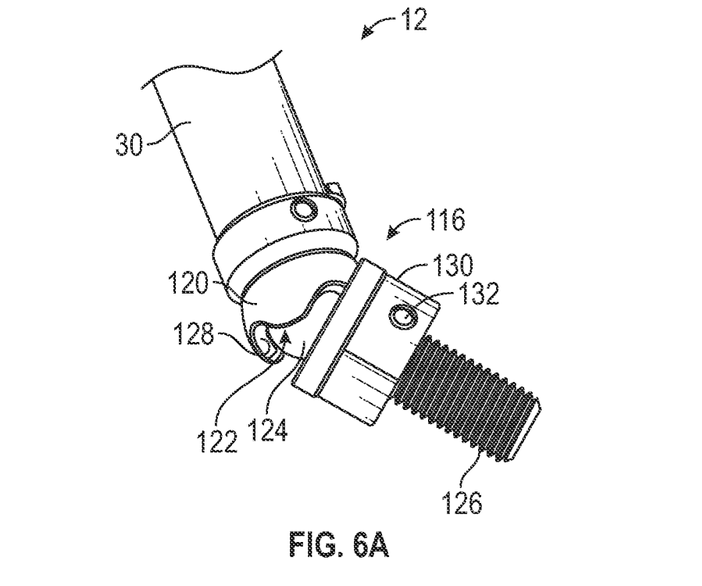
FIG. 6A is a perspective view of an exemplary polyaxial stud joint in accordance with the present disclosure.
Figure 6B:
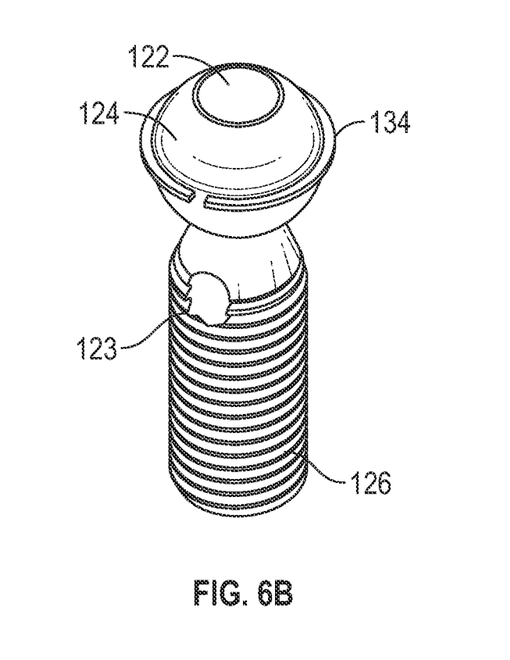
FIG. 6B is a perspective view of an exemplary spring clip positioned on a ball member in accordance with the present disclosure.
Figure 6C:
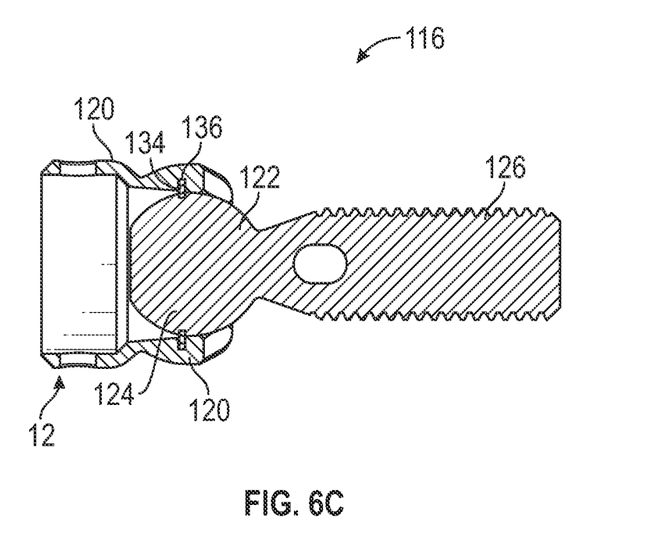
FIG. 6C is a cross-sectional view of an exemplary polyaxial stud joint in accordance with the present disclosure.

Referring to FIGS. 6B and 6C, in some embodiments, the polyaxial stud joint 116 may include a spring clip member 134. The spring clip member 134 may be configured to create friction between the ball member 124 as the ball member 124 rotates within the ball joint body 120 and further may be configured to maintain an adjustable position of the ball member 124 within the ball joint body 120. In some embodiments, the spring clip member 134 may be C-shaped clip, however, it should be understood that the spring clip member 134 may be any shape including circular, rectangular, C-shaped, serpentine, or any fanciful shape. In some embodiments, the ball member 124 may be configured to fit within the opening of the spring clip member 134 as shown in FIG. 6B.

Referring to FIG. 6C, the ball joint body 120 may include a channel 136 sized to accommodate the spring clip member 134. The ball member 124 of the ball joint stud member 122 may be rotatably accommodated by the spring clip member 134. During use, the ball joint stud member 122 may be moved by the surgeon within the spring clip member 134. The spring clip member 134 may be configured to create friction between the ball member 124 and the ball joint body 120 as the ball member 124 is rotated in the ball joint body 120 to maintain an adjustable position of the ball member 124 within the ball joint body 120.

In some embodiments, the spring clip member 134 may be integrated into any layer of the polyaxial stud joint 116. In some embodiments, a plurality of spring clip members 134 may be integrated into layers of the polyaxial stud joint 116. In some embodiments, the spring clip member 134 may be positioned in one or more grooves of the ball member 124 and interface with a surface of the ball joint body 120.

In some embodiments, the amount of friction created by the spring clip member 134 may be a function of contact surface coefficient and any normal forces created by the spring clip member 134. In some embodiments, the spring clip member 134 may be any device that effectively creates friction between the ball member 124 and the ball joint body 120.

Figure 7:
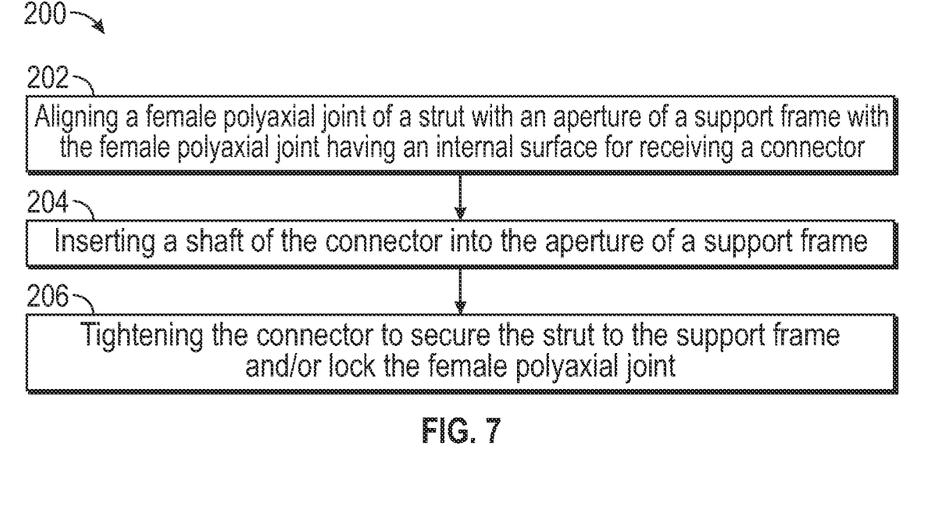
FIG. 7 is a flow chart of an exemplary method of attaching a female polyaxial joint to a support frame in accordance with the present disclosure.

FIG. 7 illustrates a flow chart 200 of an exemplary method of attaching the female polyaxial joint 16 to the support frame 14. The female polyaxial joint 16 includes the internal surface 18 for receiving the connector 20, which in this example will be described as a threaded connector, such as a screw or a bolt. In a step 202, the female polyaxial joint 16 may be aligned with the aperture 22 on second side 26 of the support frame 14. In a step 204, the shaft 21 of the connector 20 may be inserted into the first side 24 of the support frame 14, through the aperture 22 to the second side 26 of the support frame 14, and into the aperture 58 of the ball member 42. As the connector 20 is turned and thereby engages with an increasing amount of the internal surface 18 (e.g., threads) of the ball member 42, friction may be created between the spherical portion 54 of the ball member 42 and the projections 60 of the ball socket 40. Additionally, as the connector 20 increasingly engages with the ball member 42, friction may be created between the projections 60 of the ball socket 40 and the collar 72 locking the female polyaxial joint 16. Friction may also be created between the collar 72 and the support frame 14 locking the strut 12 to the support frame 14 of the external fixator device 10. In a step 206, the connector 20 may be tightened (e.g., rotated) such that the strut 12 is secured to the support frame 14 and the female polyaxial joint 16 is locked.

In some embodiments, the ball member 42 may be configured such that the ball member 42 does not contact the support frame 14 during use (i.e., a gap exists between the ball member 42 and the support frame 14 during use). In some embodiments, the ball member shaft 56 of the ball member 42 may traverse the aperture 22 of the support frame 14. In some embodiments, the ball member 42 and the collar 72 may be rotationally keyed and captivated with an interference fit (e.g., stepped fit or captive fit).

Figure 8:
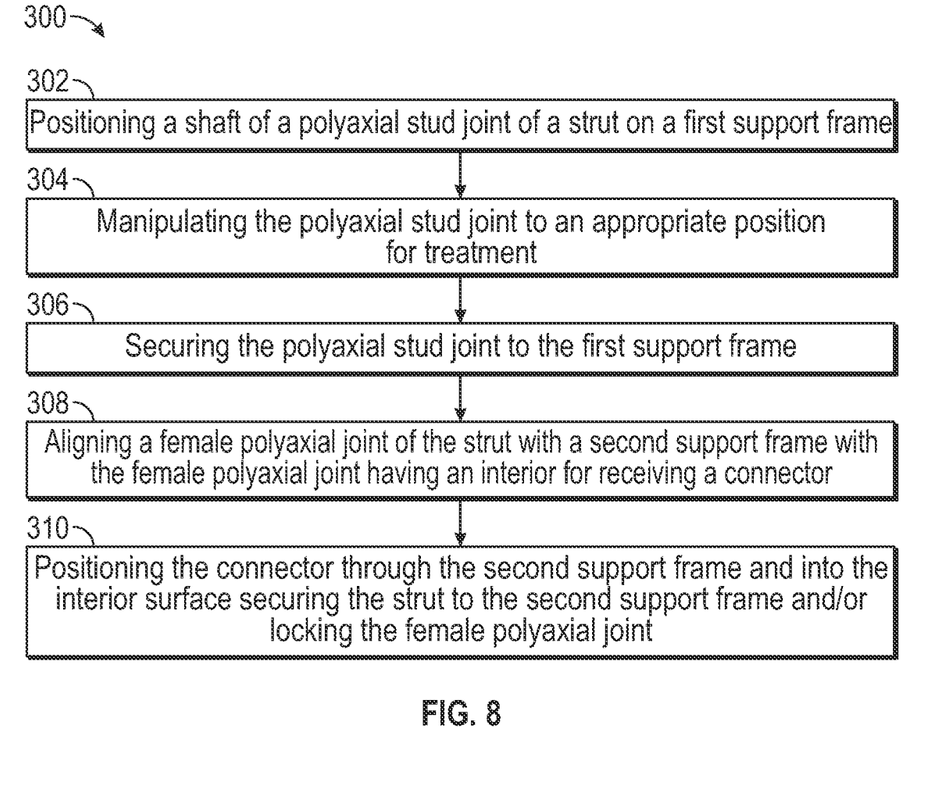
FIG. 8 is a flow chart of an exemplary method of positioning a strut between a first support frame and a second support frame in accordance with the present disclosure.

FIG. 8 illustrates a flow chart 300 of an exemplary method for positioning the strut 12 between a first support frame 14*a* having a first aperture 20*a* and a second support frame 14*b* having a second aperture 20*b*. The first end 32 of the strut 12 includes the female polyaxial joint 16 having the internal surface 18. The second end 34 of the strut 12 includes the polyaxial stud joint 116. In a step 302, the shaft 126 of the polyaxial stud joint 116 on the second end 34 of the strut 12 may be positioned within the first aperture 22 of the first support frame 14. The shaft 126 may be positioned such that the shaft 126 traverses the first aperture 22 from the second side 26 of the first support frame 14 to the first side 24 of the first support frame 14. In a step 304, the polyaxial stud joint 116 may be manipulated to an appropriate position for treatment. In a step 306, the polyaxial stud joint 116 may be secured to the first support frame 14 (e.g., securing a nut to the shaft 126 of the polyaxial stud joint 116). In a step 308, the female polyaxial joint 16 may be aligned with a second aperture 22*b* of the second support frame 14. In a step 310, the connector 20 may be positioned through the second aperture 20*b* of the second support frame 14 into the aperture 58 of the ball member 42 of the female polyaxial joint 16 having the internal surface 18 securing the strut 12 to the second support frame 14.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An external fixation device, comprising:
  at least one support frame having at least one aperture extending from a first surface to a second surface;
  a connector having a shaft configured to be received in the at least one aperture;
  at least one strut having a housing extending between a first end and a second end, the strut comprising a female polyaxial joint positioned on the first end of the at least one strut, the female polyaxial joint having a ball member with an internal surface configured to engage with the shaft of the connector and secure the strut to the at least one support frame.

2. The external fixation device of claim 1, the female polyaxial joint includes:
a ball socket; and,
wherein the ball member is rotatably coupled to the ball socket and configured to provide pivoting movement between the strut and the at least one support frame.

3. The external fixation device of claim 2, wherein the ball member includes a first end forming a spherical portion and a ball member shaft extending from the spherical portion to a second end of the ball member.

4. The external fixation device of claim 3, wherein the ball member shaft is configured to extend through the at least one aperture of the at least one support frame.

5. The external fixation device of claim 3, wherein the ball member includes an aperture positioned at the second end of the ball member and extending through the ball member shaft, the aperture providing access to the internal surface configured to engage with the shaft of the connector, the connector being threaded.

6. The external fixation device of claim 5, wherein the aperture extends through the ball member shaft and at least a portion of the spherical portion of the ball member.

7. The external fixation device of claim 2, wherein the ball socket is configured to partially enclose the ball member such that the ball member is operably received within the ball socket while maintaining rotational movement.

8. The external fixation device of claim 2, wherein the ball socket includes at least one projection providing an enclosure to receive the ball member.

9. The external fixation device of claim 2, wherein the ball socket is formed in the first end of the strut.

10. The external fixation device of claim 2, wherein the female polyaxial joint further comprises a collar positioned between the ball socket and the at least one support frame.

11. The external fixation device of claim 10, wherein the collar is configured to provide a gap between the ball member and the at least one support frame.

12. The external fixation device of claim 10, wherein the collar and the ball member are positioned via a captive fit.

13. The external fixation device of claim 12, wherein the collar has an internal side and the ball member has an external side configured to engage with the internal side of the collar in a complimentary relationship forming a lock and key anti-rotation fit.

14. The external fixation device of claim 1, wherein the at least one strut includes the female polyaxial joint positioned on the first end of the strut and a second female polyaxial joint positioned on the second end of the strut.

15. The external fixation device of claim 1, wherein the at least one strut includes the female polyaxial joint positioned on the first end of the strut and a polyaxial stud joint positioned on the second end of the strut.

16. A polyaxial joint for connecting a strut to a support frame of an external fixation device, comprising:
a ball socket; and,
a ball member having a first end with a spherical portion and a ball member shaft extending from the spherical portion to a second end of the ball member, at least one aperture positioned at the second end of the ball member and traversing through at least a portion of the ball member shaft, an internal surface of the ball member shaft being threaded and configured to receive a threaded connector extending through the support frame of the external fixation device from a first surface to a second surface.

17. The polyaxial joint of claim 16, wherein the spherical portion of the ball member is rotatably coupled to the ball socket and configured to provide pivoting movement between the strut and the support frame of the external fixation device.

18. The polyaxial joint of claim 17, further comprising a collar positioned on and surrounding the ball member shaft.

19. The polyaxial joint of claim 18, wherein the collar extends beyond the ball member shaft.

20. A method, comprising:
aligning a female polyaxial joint on a strut with an aperture within a support frame of an external fixation device, the female polyaxial joint having a ball member with an aperture providing access to an internal surface configured to receive a connector;
inserting a shaft of the connector into the aperture of the support frame and into the aperture of the ball member; and,
tightening the connector to secure the strut to the support frame and lock the female polyaxial joint.

* * * * *